United States Patent
Hirata et al.

(10) Patent No.: US 12,337,469 B2
(45) Date of Patent: Jun. 24, 2025

(54) FLEXIBLE STRUCTURE

(71) Applicant: NHK SPRING CO., LTD., Kanagawa (JP)

(72) Inventors: Takafumi Hirata, Kanagawa (JP); Yuki Hotoda, Kanagawa (JP); Yuki Hayakawa, Kanagawa (JP); Yuta Ishiyama, Kanagawa (JP)

(73) Assignee: NHK SPRING CO., LTD., Kanagawa (JP)

( * ) Notice: Subject to any disclaimer, the term of this patent is extended or adjusted under 35 U.S.C. 154(b) by 0 days.

(21) Appl. No.: 18/291,910

(22) PCT Filed: Jul. 20, 2022

(86) PCT No.: PCT/JP2022/028171
§ 371 (c)(1),
(2) Date: Jan. 24, 2024

(87) PCT Pub. No.: WO2023/008274
PCT Pub. Date: Feb. 2, 2023

(65) Prior Publication Data
US 2024/0351224 A1    Oct. 24, 2024

(30) Foreign Application Priority Data
Jul. 27, 2021    (JP) ................. 2021-122593

(51) Int. Cl.
*B25J 18/06*    (2006.01)
*B25J 9/10*    (2006.01)

(52) U.S. Cl.
CPC ............. *B25J 18/06* (2013.01); *B25J 9/104* (2013.01)

(58) Field of Classification Search
CPC .......... B25J 9/104; B25J 9/1045; B25J 18/06
See application file for complete search history.

(56) References Cited

U.S. PATENT DOCUMENTS 5,154,705 A * 10/1992 Fleischhacker .... A61B 17/3207
600/585
2020/0323600 A1* 10/2020 Kurokawa ............. A61B 17/29
(Continued)

FOREIGN PATENT DOCUMENTS

| CN | 111203912 | 5/2020 |
| CN | 112847429 | 5/2021 |

(Continued)

OTHER PUBLICATIONS

"Search Report of Europe Counterpart Application", issued on Oct. 31, 2024, p. 1-p. 8.

(Continued)

*Primary Examiner* — Bobby Rushing, Jr.
(74) *Attorney, Agent, or Firm* — JCIPRNET

(57) ABSTRACT

A flexible structure includes a first member, a second member, a recess, and a wire. The first member is capable of flexing and extending. The second member covers an outer circumference of the first member and is capable of flexing and extending in conjunction with the first member. The recess is provided at an inner circumference of the second member. The wire is held between the first member and the second member in a state in which at least a part of the wire is inserted into the recess in the radial direction.

12 Claims, 3 Drawing Sheets

(56) References Cited

U.S. PATENT DOCUMENTS

2021/0186637 A1* 6/2021 Kurokawa .............. F16H 21/44
2021/0307773 A1* 10/2021 Hirata ................ A61B 17/2909

FOREIGN PATENT DOCUMENTS

| JP | 2020172001 | 10/2020 |
|---|---|---|
| JP | 2020172003 | 10/2020 |
| WO | 2019073860 | 4/2019 |

OTHER PUBLICATIONS

"International Preliminary Report on Patentability of PCT/JP2022/028171; this report contains the following items: Form PCT/IB/326, PCT/IB/338, PCT/IB/373, PCT/ISA237(cover sheet), PCT/ISA237(Box No. I), PCT/ISA237(Box No. V)", mailed on Feb. 8, 2024, Jan. 18, 2024 and Sep. 6, 2022, which is English translation of "Written Opinion of the International Searching Authority", p. 1-p. 11.

"International Search Report (Form PCT/ISA/210) of PCT/JP2022/028171", mailed on Sep. 6, 2022, with English translation thereof, pp. 1-4.

"Office Action of Taiwan Counterpart Application", issued on Mar. 13, 2023, with English translation thereof, pp. 1-13.

* cited by examiner

FLEXIBLE STRUCTURE

CROSS-REFERENCE TO RELATED APPLICATION

This application is a 371 application of the International PCT application serial no. PCT/JP2022/028171, filed on Jul. 20, 2022, which claims the priority benefits of Japan Patent Application No. 2021-122593, filed on Jul. 27, 2021. The entirety of each of the above-mentioned patent applications is hereby incorporated by reference herein and made a part of this specification.

TECHNICAL FIELD

The present invention relates to a flexible structure realizing a joint function of a robot or the like.

RELATED ART

Flexible structures having a joint function enabling flexing and extending are included in robots, manipulators, or actuators. For example, a flexible structure for realizing such a joint function is described in Patent Document 1.

The flexible structure of Patent Document 1 includes an elastic member as a first member and a flexible member as a second member covering the outer circumference of the elastic member. This flexible structure flexes in response to pulling of drive wires.

The drive wires are inserted into insertion holes provided at each of a plurality of wave washers constituting the flexible member so that the drive wires are guided and their circumferential displacement is restricted. Accordingly, a defective action of the flexible structure is suppressed.

However, in such a configuration, it is required to secure a predetermined width on inner and outer sides in the radial direction with respect to the insertion hole of the wave washer. Thus, in the conventional flexible structures, there is a limitation on reduction in the outer diameter or increase in the inner diameter of the flexible member.

Such an issue is not limited to flexible structures with flexible members composed of wave washers, but occurs widely among flexible structures that guide cord-shaped members such as drive wires by insertion holes or the like.

RELATED ART DOCUMENTS

Patent Documents

Patent Document 1: Japanese Patent Application Laid-Open No. 2020-172001

SUMMARY OF INVENTION

Problem to be Solved by Invention

The problem to be solved is the limitation on reduction in an outer diameter or increase in an inner diameter of a second member covering an outer circumference of a first member.

Means for Solving Problem

The present invention provides a flexible structure including a first member, a second member, a recess, and a cord-shaped member. The first member is capable of flexing and extending. The second member covers an outer circumference of the first member and is capable of flexing and extending in conjunction with the first member. The recess is provided in a radial direction at at least one of the first member and the second member. The cord-shaped member is held between the first member and the second member in a state in which at least a part of the cord-shaped member is inserted into the recess in the radial direction.

Effects of Invention

According to the present invention, it is possible to reduce the outer diameter or increase the inner diameter of the second member covering the outer circumference of the first member.

DESCRIPTION OF EMBODIMENTS

Figure 1:
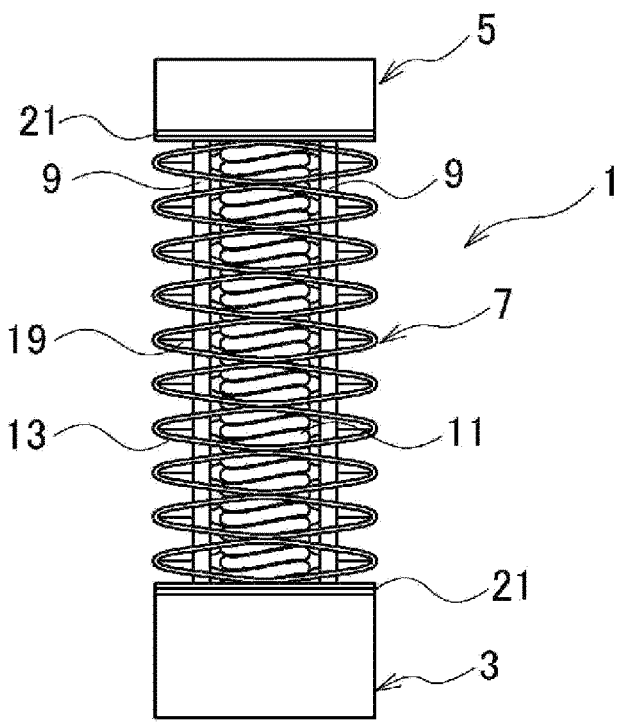
FIG. 1 is a front view showing a flexible structure according to Embodiment 1 of the present invention.

An objective of reducing an outer diameter or increasing an inner diameter of a second member covering an outer circumference of a first member is realized by providing a recess, into which at least a part of a cord-shaped member is inserted, at at least one of the first member and the second member.

That is, a flexible structure (1) includes a first member (11), a second member (13), a recess (23), and a cord-shaped member (9). The first member (11) is capable of flexing and extending. The second member (13) covers an outer circumference of the first member (11) and is capable of flexing and extending in conjunction with the first member (11). The recess (23) is provided in a radial direction at at least one of the first member (11) and the second member (13). The cord-shaped member (9) is held between the first member (11) and the second member (13) in a state in which at least a part of the cord-shaped member (9) is inserted into the recess (23) in the radial direction.

At least one of the first member (11) and the second member (13) may be formed in a tubular shape, and the recess (23) may be a groove provided at at least one of the first member (11) and the second member (13) formed in the tubular shape.

In a case where the recess (23) is a groove, the second member (13) may have a tubular shape formed by joining a plurality of wave washers (19) in an axial direction, and the recess (23) may be provided at each of the wave washers (19) continuous in the axial direction.

The recess (23) may accommodate and hold a plurality of cord-shaped members (9). In that case, the plurality of cord-shaped members (9) in the recess (23) may configured to be arranged along a circumferential direction according to a shape of the recess (23).

Embodiment 1

[Flexible Structure]

Figure 2:
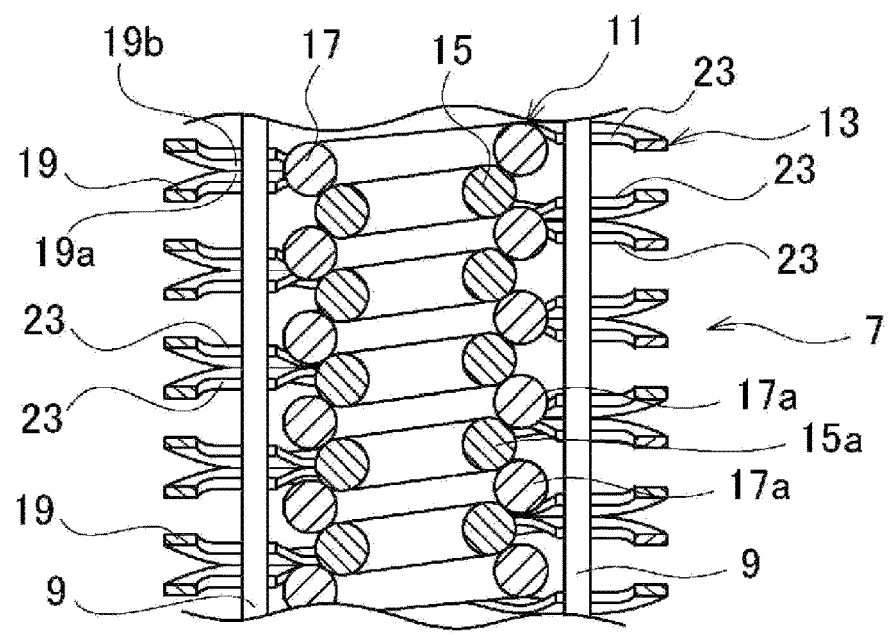
FIG. 2 is a cross-sectional view partially showing a flexing part of the flexible structure in FIG. 1.
Figure 3:
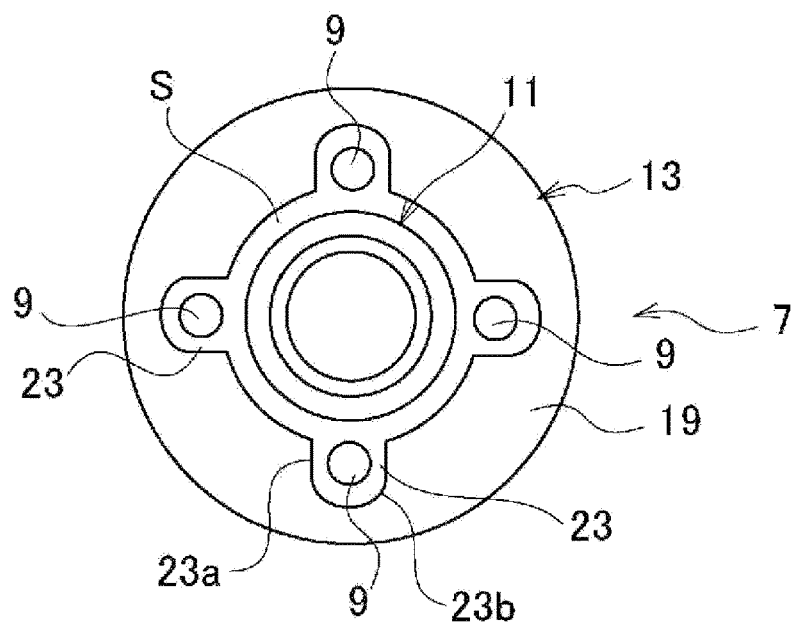
FIG. 3 is a plan view showing the flexing part of the flexible structure in FIG. 1.

FIG. 1 is a front view showing a flexible structure according to Embodiment 1 of the present invention. FIG. 2 is a cross-sectional view partially showing a flexing part of the flexible structure. FIG. 3 is a plan view showing the flexing part of the flexible structure.

The flexible structure 1 is applicable to joint function parts of various machines for medical or industrial use, such as manipulators, robots, and actuators. The joint function part is an apparatus, a mechanism, a device, etc. having a function as a joint that flexes and extends.

The flexing and extending refer to flexing and extending with respect to the axial direction. The axial direction is a direction along the axis of the flexible structure 1, but it does not need to be strictly interpreted and also includes a direction slightly inclined with respect to the axis of the flexible structure 1.

This flexible structure 1 includes a base part 3 and a movable part 5, a flexing part 7, and a wire 9 serving as a cord-shaped member.

The base part 3 and the movable part 5 are each composed of a columnar body, e.g., a cylindrical body, formed of an appropriate material such as metal or resin. The base part 3 and the movable part 5 are not limited to columnar bodies, but may be in any appropriate forms depending on the machine to which the flexible structure 1 is applied.

The movable part 5 is supported at the base part 3 by the flexing part 7, and is capable of displacing in the axial direction.

The flexing part 7 includes a first member 11 and a second member 13.

The first member 11 is a member capable of flexing and extending. This first member 11 functions as a core member, and suppresses axial compression of the flexing part 7.

In this embodiment, the first member 11 has a double coil structure in a tubular shape, and is composed of an inner coil part 15 and an outer coil part 17. This first member 11 is capable of flexing and extending elastically, and is capable of withstanding axial compression.

The first member 11 may be, for example, a single close-contact coil, a tubular body made of resin, or other flexible tubular bodies capable of withstanding axial compression. This first member 11 does not need to have elasticity as long as it has flexibility for flexing and extending.

Also, the first member 11 may be capable of compression in the axial direction like a compression coil spring as long as compression between the base part 3 and the movable part 5 is suppressed to an extent.

In this embodiment, the inner coil part 15 and the outer coil part 17 are respectively coil springs having elasticity capable of flexing with respect to the axial direction. The materials of the inner coil part 15 and the outer coil part 17 may be any appropriate materials such as metal or resin depending on the machine to which the flexible structure 1 is applied. The cross-sectional shapes of the bare wires of the inner coil part 15 and the outer coil part 17 are circular shapes having the same wire diameter, but may also be semicircular or elliptical. The cross-sectional shapes, wire diameters, etc. of the inner coil part 15 and the outer coil part 17 may also be different from each other.

The inner coil part 15 has a central diameter smaller than the outer coil part 17 and is screwed into the outer coil part 17. Accordingly, a winding part 15a of the inner coil part 15 fits between adjacent winding parts 17a of the outer coil part 17. This fitting is maintained not only when the first member 11 is in a straight shape but also when it is flexing, and is capable of suppressing axial compression of the flexing part 7.

The central diameters of the inner coil part 15 and the outer coil part 17 are constant from one end to the other end in the axial direction, but may also be changed in the axial direction.

In such a first member 11 having a double coil structure, during flexing, the gap between adjacent winding parts 17a of the outer coil part 17 decreases on the inner side of flexing, and the gap between adjacent winding parts 17a of the outer coil part 17 increases on the outer side of flexing.

Accordingly, the length in the axis of the outer coil part 17 of the first member 11 during flexing does not change compared to when being in a straight shape. Thus, in the case where the first member 11 is used to guide a flexible member such as a push-pull cable movably in the axial direction on its inner circumferential side, it is possible to keep the path length of the flexible member constant.

The second member 13 is a member that covers the outer circumference of the first member 11 and is capable of flexing and extending in conjunction with the first member 11. In this embodiment, the second member 13 is configured in a tubular shape as a whole by stacking a plurality of wave washers 19 in the axial direction. This second member 13 is capable of flexing due to elastic deformation of the wave washers 19.

The second member 13 may be configured by a double coil structure, bellows, other tubular bodies, etc. Also, the second member 13 may also be a compression coil spring or the like.

Each wave washer 19 is formed in an annular shape. Between wave washers 19 adjacent in the axial direction, a peak part 19a of one wave washer 19 abuts against a valley part 19b of the other wave washer 19. The peak part 19a and the valley part 19b which abut against each other are joined together by an appropriate means such as welding or adhesion.

A plurality of flat washers 21 having a deformation amount smaller than the wave washer 19 are attached at both axial ends of the second member 13. The base part 3 and the movable part 5 are joined to both ends of the second member 13 via these flat washers 21. This joining is performed by an appropriate means such as welding. The flat washers 21 may also be omitted.

A plurality of recesses 23 guiding the wires 9 respectively are formed in the radial direction at such a second member 13. The radial direction refers to a direction along the diameter of the flexible structure 1, but also includes a direction slightly inclined with respect to the diameter of the flexible structure 1.

The plurality of recesses 23 are arranged at the inner circumference of the second member 13 at equal intervals in the circumferential direction. In this embodiment, the recess 23 is provided every 90 degrees in the circumferential direction. However, the number of the recesses 23 may be changed such that the recess 23 is arranged every 60 degrees, every 120 degrees, every 180 degrees, etc. in the circumferential direction. Also, the interval between the plurality of recesses 23 does not have to be equal but may also vary. The circumferential direction refers to a direction along the outer circumference of the flexible structure 1.

These recesses 23 are provided at each of the wave washers 19 which are continuous in the axial direction. Thus, the recesses 23 reduce the thickness of the wave washer 19 in the radial direction and reduce the rigidity of the wave washer 19 and the second member 13.

In this embodiment, the recesses 23 are provided at all the wave washers 19 and the flat washers 21 which are continuous in the axial direction. However, the recesses 23 may also be provided only at a part of the wave washers 19. Thus, it is possible to provide the recesses 23 at a part or an entirety of the axial direction of the second member 13. In the case where the recesses 23 are provided at a part of the axial direction of the second member 13, the inner diameter of the wave washers without the recesses may be configured larger than the inner diameter of the wave washers 19 with the recesses 23.

The corresponding recesses 23 between the wave washers 19 communicate with each other in the axial direction and, as a whole, form a groove along the axial direction provided at the inner circumference of the second member 13 in a tubular shape.

However, the corresponding recesses 23 between the wave washers 19 may also be shifted in the circumferential direction to form a spiral groove or the like as a whole.

Each recess 23 is opened at the inner circumference of the wave washer 19 of the second member 13 and faces a space between the first member 11 and the second member 13. In this embodiment, in a plan view, each recess 23 is composed of a straight part 23a on the inner circumferential side along the radial direction and a semicircular part 23b on the outer circumferential side continuous with the straight part 23a.

The recess 23 may have at least a part that forms a concave shape in the radial direction, and it is not required that the entirety of the recess 23 has a concave shape along the radial direction. Thus, the recess 23 may also be provided along a direction inclined with respect to the radial direction as a whole.

Furthermore, since the recesses 23 may be provided at at least one of the first member 11 and the second member 13, it is possible to provide the recesses 23 not only at the inner circumference of the second member 13, but also at the outer circumference of the first member 11 or at both the outer circumference of the first member 11 and the inner circumference of the second member 13.

In the case of providing the recesses at both the outer circumference of the first member 11 and the inner circumference of the second member 13, the recesses of the first member 11 and the second member 13 may face each other in the radial direction to form one recess, or the recesses of the first member 11 and the second member 13 may be shifted in the circumferential direction to each form one recess.

A tip part of the wire 9 is attached to the movable part 5 and passes through the flexing part 7, and a base end part of the wire 9 is connected to an operation mechanism (not shown) or the like. By pulling this wire 9 in the axial direction, the movable part 5 is driven to flex the flexible structure 1.

In this embodiment, a plurality of wires 9 are provided, and by pulling one or more wires 9, it is possible to flex the flexing part 7 with respect to all directions in 360° in a plan view. The number of the wires 9 driving the movable part 5 may be appropriately set depending on the required flexing action of the flexible structure 1.

Such a wire 9 is guided by the recesses 23 in the flexing part 7, and displacement of the wire 9 in the circumferential direction is restricted. That is, the wire 9 is held between the first member 11 and the second member 13 in a state in which at least a part of the wire 9 is inserted into the recess 23 in the radial direction.

By guiding the wire 9 with the recesses 23 facing a space between the first member 11 and the second member 13 in this manner, compared to the case of conventional insertion holes, it is possible to increase the inner diameter of the second member 13 with the outer diameter unchanged, or to decrease the outer diameter of the second member 13 with the inner diameter unchanged.

In this embodiment, the cross-sectional shape of the wire 9 is a circular shape, and this circular shape is all inserted into the recess 23. A gap S in the radial direction between the first member 11 and the second member 13 is formed smaller than the diameter of the wire 9, and circumferential displacement of the wire 9 inserted into the recess 23 is suppressed.

It is also possible that the wire 9 is slightly inserted into the recess 23 in the radial direction to suppress circumferential displacement. Thus, the recess 23 may have an appropriate shape depending on the insertion amount of the wire 9. Also, as long as circumferential displacement can be suppressed by the recess 23, the cross-sectional shape of the wire 9 may also be elliptical or rectangular.

The wire 9 preferably has flexibility to a degree that does not hinder the flexing and extending of the flexible structure 1. The wire 9 may also be made of metal applied with an insulating coating to constitute an electrical conduction path. The cord-shaped member is not limited to the wire 9, but may also be a stranded wire, a single wire, a piano wire, a multi-joint rod, a chain, a string, a thread, a rope, etc.

[Action and Others]

In this embodiment, the flexible structure 1 makes it possible for an operator to pull any one or more wires 9 and direct the movable part 5 to a desired direction.

At this time, since the wire 9 is held between the first member 11 and the second member 13 in a state in which a part of the wire 9 is inserted into the recess 23, circumferential displacement is restricted. As a result, the wire 9 is pulled at an appropriate position, a defective action of the flexible structure 1 is suppressed, and the action becomes stable.

When the wire 9 is pulled to flex the flexible structure 1, since the length of the central part of the first member 11 does not change, the path length of the member passing through the inside and the action of the flexible structure 1 become more stable.

Also, before and after flexing, with the corresponding winding part 15a of the inner coil part 15 continuously fitted between adjacent winding parts 17a of the outer coil part 17 of the first member 11, axial compression of the flexible structure 1 is suppressed, and the path length of the member passing through the inside and the action of the flexible structure 1 become more stable.

The second member 13 flexes in conjunction with the first member 11 due to elastic deformation of the wave washers 19. At this time, since the rigidity of each wave washer 19 of the second member 13 is reduced by the recesses 23, the flexible structure can be flexed with a smaller force.

Effect of Embodiment 1

As described above, the flexible structure 1 of this embodiment includes: the first member 11 capable of flexing and extending; the second member 13 covering the outer circumference of the first member 11 and capable of flexing and extending in conjunction with the first member 11; the recess 23 provided at the inner circumference of the second member 13; and the wire 9 held between the first member 11 and the second member 13 in a state in which at least a part of the wire 9 is inserted into the recess 23 in the radial direction.

Thus, in the flexible structure 1, with the wire 9 guided by the recess 23, the action becomes stable. Moreover, in the flexible structure 1, compared to the case of guiding with conventional insertion holes, it is possible to reduce the outer diameter or increase the inner diameter of the second member 13 covering the outer circumference of the first member 11.

Also, in the flexible structure 1, it is possible to reduce the rigidity of the second member 13 by the recess 23, and it is possible to flex the flexible structure with a smaller force.

Since the recess 23 is a groove provided at the inner circumference of the second member 13 formed in a tubular shape, it is possible to reliably guide the wire 9.

The second member 13 has a tubular shape formed by stacking a plurality of wave washers 19 in the axial direction, and the recess 23 is provided at the wave washers 19 continuous in the axial direction.

Thus, in this embodiment, it is possible to easily form the recess 23 on the wave washers 19 by pressing or the like, and by stacking the wave washers 19 having the recess 23, it is possible to easily form the recess 23 as a groove at a desired position in the axial direction of the second member 13.

Embodiment 2

Figure 4:
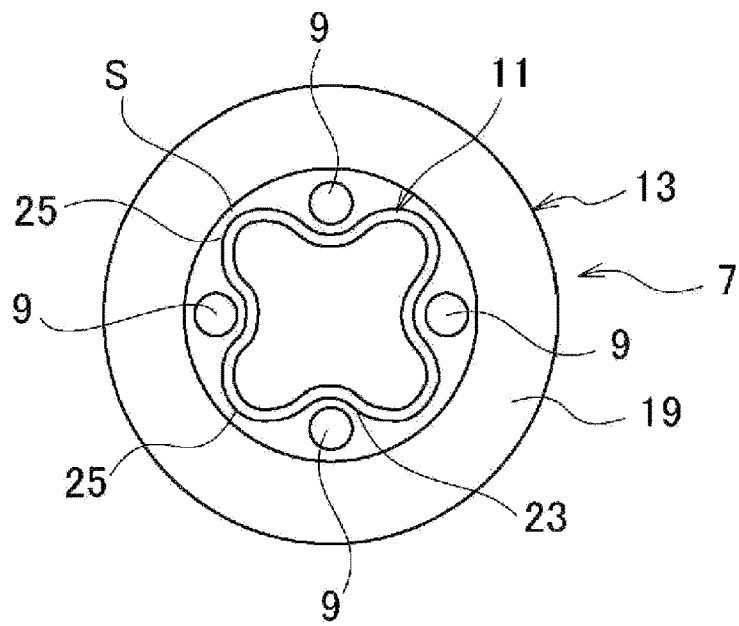
FIG. 4 is a plan view showing a flexing part of a flexible structure according to Embodiment 2 of the present invention.

FIG. 4 is a plan view showing a flexible structure according to Embodiment 2 of the present invention. In Embodiment 2, configurations corresponding to those in Embodiment 1 are labeled with the same reference signs, and repeated descriptions thereof will be omitted.

In this embodiment, the recess 23 is provided at the first member 11. Thus, the second member is configured by stacking wave washers 19 in an annular shape without the recess 23. The rest is identical to Embodiment 1.

The first member 11 is a flexible member in a tubular shape and includes a plurality of recesses 23 at the outer circumference. The recesses 23 are set according to the cross-sectional shape of the first member 11. The recess 23 of this embodiment is formed by a concave curved surface of the first member 11. Adjacent to the recess 23, a protrusion 25 composed of a convex curved surface is provided at the first member 11. A space between the protrusion 25 and the inner circumference of the second member 13 forms a gap S smaller than the diameter of the wire 9.

In such Embodiment 2 as well, the same effects as in Embodiment 1 can be achieved. Also, in the embodiment, since the recess 23 is provided at the first member 11, it is possible to free set the radial width of the second member 13, and it is possible to reduce the outer diameter or increase the inner diameter of the second member 13.

Embodiment 3

Figure 5:
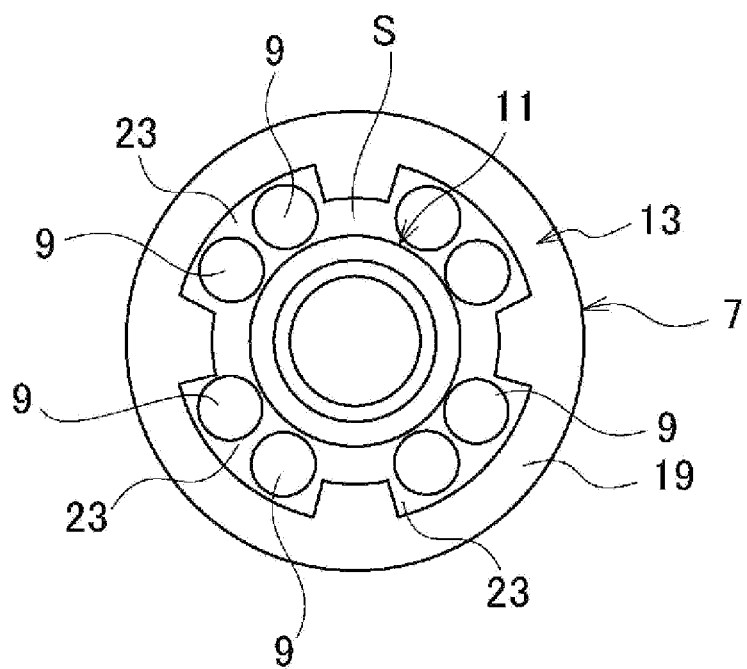
FIG. 5 is a plan view showing a flexing part of a flexible structure according to Embodiment 3 of the present invention.

FIG. 5 is a plan view showing a flexible structure according to Embodiment 3 of the present invention. In Embodiment 3, configurations corresponding to those in Embodiment 1 are labeled with the same reference signs, and repeated descriptions thereof will be omitted.

In this embodiment, the recess 23 is provided at the second member 13, and a plurality of wires 9 are accommodated and held in this recess 23. The rest is identical to Embodiment 1.

Each recess 23 has a fan-shaped concave shape, and a plurality of wires 9 are arranged along the circumferential direction according to the shape of this recess 23.

The recess 23 of this embodiment accommodates two wires 9 arranged along the circumferential direction, and allows a part of the wires 9 in the radial direction (about half in the radial direction in this embodiment) to be inserted.

The plurality of wires 9 in each recess 23 are a combination of a plurality of operational wires for operating the movable part 5, or a combination of an operational wire 9 and its guide wire or a wire for an electrical conduction path.

In such Embodiment 3, by enlarging the recess 23 compared to Embodiment 1, the function of the flexible structure 1 can be enhanced with the plurality of wires 9. Furthermore, in Embodiment 3 as well, the same effects as in Embodiment 1 can be achieved.

The invention claimed is:

1. A flexible structure comprising:
a first member capable of flexing and extending;
a second member that covers an outer circumference of the first member and is capable of flexing and extending in conjunction with the first member;
a first recess provided in a radial direction at the first member; and
a first cord-shaped member held between the first member and the second member in a state in which at least a part of the first cord-shaped member is inserted into the first recess in the radial direction,
wherein the first recess is recessed radially inward from an outer circumferential surface of the first member.

2. The flexible structure according to claim 1, wherein the first member is formed in a tubular shape, and the first recess is a first groove provided at the first member formed in the tubular shape.

3. The flexible structure according to claim 1, wherein the second member has a tubular shape formed by stacking a plurality of wave washers in an axial direction.

4. The flexible structure according to claim 1, further comprising:
a second recess provided in the radial direction at the first member;
a second cord-shaped member held between the first member and the second member in a state in which at least a part of the second cord-shaped member is inserted into the second recess in the radial direction.

5. The flexible structure according to claim 4, wherein the first cord-shaped member is arranged along a circumferential direction according to a shape of the first recess,
the second cord-shaped member is arranged along the circumferential direction according to a shape of the second recess.

6. A flexible structure comprising:
a first member capable of flexing and extending;
a second member that covers an outer circumference of the first member and is capable of flexing and extending in conjunction with the first member;
a first recess provided in a radial direction at the second member; and
a first cord-shaped member held between the first member and the second member in a state in which at least a part of the first cord-shaped member is inserted into the first recess in the radial direction,
wherein the first recess is recessed radially outward from an inner circumferential surface of the second member.

7. The flexible structure according to claim 6, wherein
the second member is formed in a tubular shape, and
the first recess is a groove provided at the second member formed in the tubular shape.

8. The flexible structure according to claim 6, wherein
the second member has the tubular shape formed by stacking a plurality of wave washers in an axial direction, and
the first recess is provided at the wave washers continuous in the axial direction.

9. The flexible structure according to claim 6, further comprising:
a second recess provided in the radial direction at the second member;
a second cord-shaped member held between the first member and the second member in a state in which at least a part of the second cord-shaped member is inserted into the second recess in the radial direction.

10. The flexible structure according to claim 9, wherein
the first cord-shaped member is arranged along a circumferential direction according to a shape of the first recess,
the second cord-shaped member is arranged along the circumferential direction according to a shape of the second recess.

11. The flexible structure according to claim 6, wherein another recess is provided in a radial direction at the first member,
wherein the another recess is recessed radially inward from an outer circumferential surface of the first member.

12. The flexible structure according to claim 6, further comprising:
another cord-shaped member, held between the first member and the second member in a state in which at least a part of the another cord-shaped member is inserted into the first recess in the radial direction.

* * * * *